(12) United States Patent
Yamaya (10) Patent No.: US 9,931,029 B2
(45) Date of Patent: Apr. 3, 2018

(54) WASHING SYSTEM (71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/430,905

(22) Filed: Feb. 13, 2017

(65) Prior Publication Data
US 2017/0150877 A1  Jun. 1, 2017

Related U.S. Application Data (63) Continuation of application No. PCT/JP2015/075913, filed on Sep. 11, 2015.

(30) Foreign Application Priority Data

Oct. 15, 2014  (JP) .................................. 2014-210881

(51) Int. Cl.
*A61B 1/12*  (2006.01)
*B08B 9/032*  (2006.01)

(52) U.S. Cl.
CPC ............ *A61B 1/123* (2013.01); *B08B 9/0321* (2013.01)

(58) Field of Classification Search
CPC ............................. A61B 1/123; B08B 9/0321
See application file for complete search history.

(56) References Cited

U.S. PATENT DOCUMENTS

| 4,763,678 | A | * | 8/1988 | Ott | A61B 1/123 |
| | | | | | 134/104.2 |
| 5,090,433 | A | * | 2/1992 | Kamaga | A61B 1/122 |
| | | | | | 134/169 C |
| 5,840,251 | A | * | 11/1998 | Iwaki | A61L 2/18 |
| | | | | | 134/104.2 |

(Continued)

FOREIGN PATENT DOCUMENTS

| JP | S58-133230 A | 8/1983 |
| JP | H03-280925 A | 12/1991 |

(Continued)

OTHER PUBLICATIONS

International Search Report dated Dec. 15, 2015 issued PCT/JP2015/075913.

(Continued)

*Primary Examiner* — Michael Barr
*Assistant Examiner* — Benjamin L Osterhout
(74) *Attorney, Agent, or Firm* — Scully, Scott, Murphy & Presser, P.C.

(57) ABSTRACT

A washing system includes a cylindrical body portion which is prepared for each kind of insertion portion and a supply hole portion which is provided in the body portion to communicate with the inside of the body portion and which supplies a fluid to an opening portion of an insertion portion housed in the body portion. The washing system includes a supply mechanism which is shared by the body portion corresponding to each insertion portion that is prepared which supplies the fluid to the supply hole portion and which is attachable to and detachable from the supply hole portion.

8 Claims, 8 Drawing Sheets (56) References Cited

U.S. PATENT DOCUMENTS

| | | | | |
|---|---|---|---|---|
| 6,132,691 | A | * | 10/2000 | Coles .................... A61L 2/18 |
| | | | | 206/210 |
| 2001/0042561 | A1 | * | 11/2001 | Kaketani ................ A61B 1/123 |
| | | | | 134/169 R |
| 2007/0112249 | A1 | * | 5/2007 | Yamaya ............. A61B 1/00098 |
| | | | | 600/107 |
| 2008/0188715 | A1 | * | 8/2008 | Fujimoto ........... A61B 1/00091 |
| | | | | 600/157 |
| 2014/0275787 | A1 | * | 9/2014 | Miyamoto ............. A61B 1/005 |
| | | | | 600/139 |

FOREIGN PATENT DOCUMENTS

| | | |
|---|---|---|
| JP | H08-196505 A | 8/1996 |
| JP | H11-151198 A | 6/1999 |

OTHER PUBLICATIONS

English translation of International Preliminary Report on Patentability dated Apr. 27, 2017 together with the Written Opinion received in related International Application No. PCT/JP2015/075913.

* cited by examiner

WASHING SYSTEM

CROSS-REFERENCE TO RELATED APPLICATIONS

This application is a Continuation Application of PCT Application No. PCT/JP2015/075913, filed Sep. 11, 2015 and based upon and claiming the benefit of priority from prior Japanese Patent Application No. 2014-210881, filed Oct. 15, 2014, the entire contents of all of which are incorporated herein by reference.

BACKGROUND OF THE INVENTION

1. Field of the Invention

The present invention relates to a washing system to wash an insertion portion of an insertion device.

2. Description of the Related Art

For example, Pat. Appln. KOKAI Publication No. 8-196505 discloses the washing to an insertion device which is, for example, an endoscope. The insertion device has an insertion portion, and a cover portion provided at a distal end portion of the insertion portion. The cover portion has a washing tool attachment opening portion.

When the distal end portion having a complex shape is washed, a fluid such as a washing solution is strongly blown to the distal end portion, and the distal end portion is preliminarily washed. A washing system used in this case has a cylindrical body portion into which the distal end portion is inserted, and a supply mechanism which is integrally attached to the body portion and which supplies the fluid to the body portion.

BRIEF SUMMARY OF THE INVENTION

An aspect according to a washing system of the invention is a washing system to wash an insertion portion of an insertion device having an opening portion provided in a distal-side circumferential surface of the insertion portion, and includes a cylindrical body portion which is prepared for each kind of insertion portion and which houses a distal end portion of the insertion portion; a supply hole portion which is provided in the body portion to communicate with the inside of the body portion and which supplies a fluid to the opening portion of the insertion portion housed in the body portion; and a supply mechanism which is shared by the body portion corresponding to each insertion portion that is prepared which supplies the fluid to the supply hole portion and which is attachable to and detachable from the supply hole portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF EMBODIMENTS

Hereinafter, an embodiment of the present invention will be described in detail with reference to the drawings.

One Embodiment

[Configuration]

One embodiment is described with reference to FIG. 1, FIG. 2A, FIG. 2B, FIG. 3, FIG. 4, FIG. 5A, FIG. 5B, FIG. 6A, FIG. 6B, FIG. 6C, FIG. 7A, and FIG. 7B. As a washing system 300 is unshown in FIG. 1, some components are unshown in some of the drawings for clarity of illustration.

[Insertion System 1]

Figure 1:
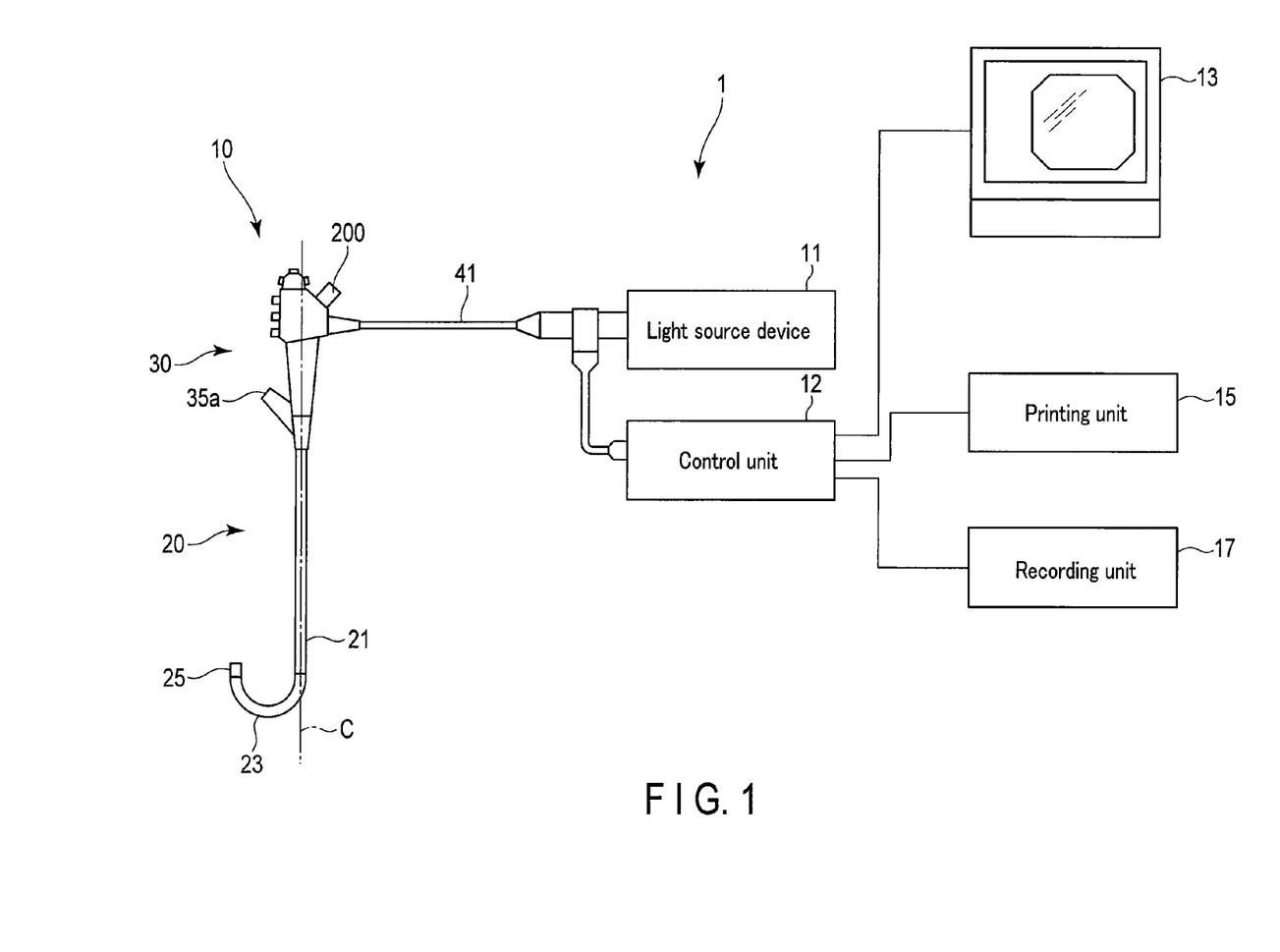
FIG. 1 is a schematic diagram of an insertion system according to one embodiment of the present invention.
Figure 2A:
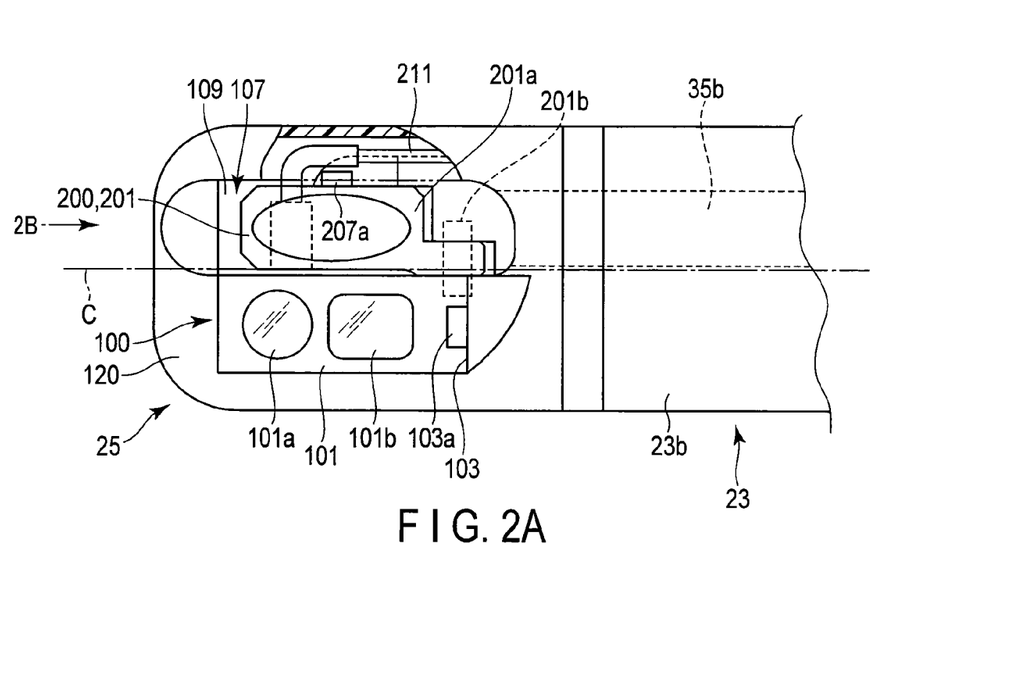
FIG. 2A is a top view of a distal configuration portion in one embodiment.
Figure 2B:
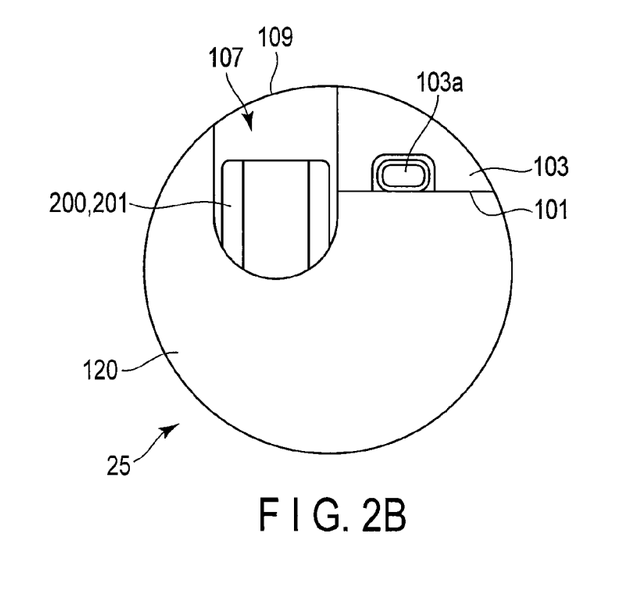
FIG. 2B is a front view of the distal configuration portion seen from an arrow 2B side shown in FIG. 2A.
Figure 3:
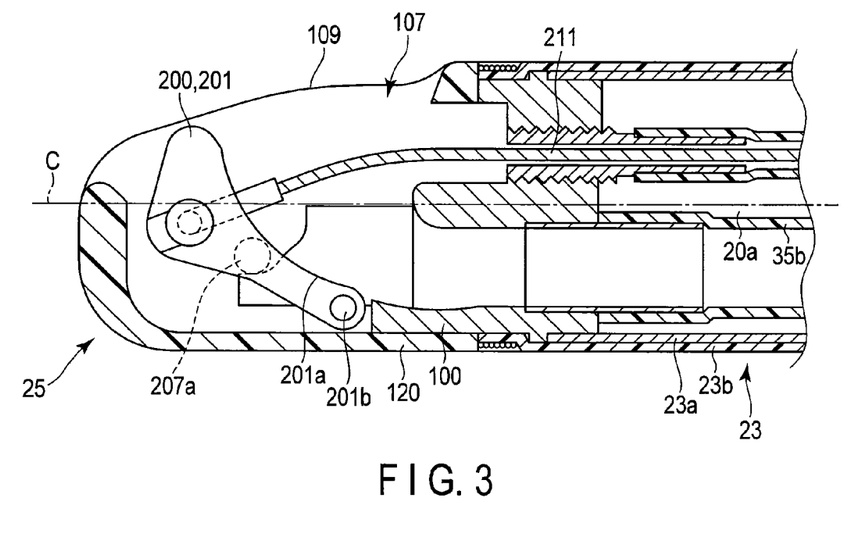
FIG. 3 is a diagram showing a swing table in a maximum falling state.

A washing target for the washing system 300 according to the present embodiment is, by way of example, a distal end portion of an insertion portion 20 including a treatment instrument swing table (hereinafter referred to as a swing table 201). The insertion portion 20 is provided in an endoscopic apparatus as an insertion system 1, and the distal end portion of the insertion portion 20 is, for example, a distal configuration portion 25. FIG. 1 is a diagram showing the configuration of the insertion system 1. FIG. 2A is a top view of the distal configuration portion 25 having the swing table 201. FIG. 2B is a diagram showing the external configuration of the distal configuration portion 25 seen from the front side of the distal configuration portion 25. FIG. 3 is a diagram showing the configuration of a cross section of the swing table 201 in a maximum falling state in the distal configuration portion 25 shown in FIG. 2A.

[Insertion Device 10]

As shown in FIG. 1, the insertion system 1 chiefly has an insertion device 10, and a light source device 11 which supplies an illumination light to the insertion device 10. The insertion system 1 has a control unit 12 including a video processor which performs image processing of a video signal imaged by an unshown imaging unit provided at the distal end portion of the insertion portion 20 to generate an observation image and image information regarding the observation image, and a display unit 13 which displays the observation image and the image information. The insertion system 1 has a printing unit 15 which prints the observation image and the image information, and a recording unit 17 which records the video signal.

Here, the insertion device 10 according to the present embodiment is, by way of example, a side-viewing medical endoscope to be inserted into a lumen such as a duodenal papilla or a biliary and pancreatic area. The insertion device 10 does not need to be limited to the side-viewing medical endoscope as long as the insertion device 10 is washed by the washing system 300 according to the present embodiment, and the insertion device 10 may be a direct-viewing medical endoscope, or may be a medical endoscope to insert a treatment instrument into a part other than the lumen, or may be an industrial endoscope. The insertion device 10 may also be, for example, a catheter or an over tube having no illumination optical system and no observation optical system. If the insertion device 10 has, in its distal end-side circumferential surface, an opening portion or a part to which a fluid for washing is supplied and the opening portion or the part is inserted into or removed from a body portion 400 of the washing system 300, the opening portion or the part can be washed by the washing system 300.

An unshown tool to be inserted into the insertion portion 20 of this insertion device 10 is referred to as an insert object. This tool includes, for example, the treatment instrument, and a guide member which guides the treatment instrument to an affected area. The treatment instrument includes a forceps.

As shown in FIG. 1, the insertion device 10 chiefly has the insertion portion 20 which extends along a longitudinal axis C direction, and an operation portion 30 to operate the insertion portion 20. The insertion portion 20 has a flexible tubular portion 21 which is coupled to the operation portion 30 and which has flexibility, a bendable portion 23 which is coupled to a distal end portion of the flexible tubular portion 21 and which can bend relative to the longitudinal axis C, and the distal configuration portion 25 which is coupled to a distal end portion of the bendable portion 23 and which houses the swing table 201. The operation portion 30 is connected to the light source device 11 and the control unit 12 by a universal cord 41. An insertion opening portion 35a to introduce the insert object into the insertion portion 20 is provided between a proximal end portion of the insertion portion 20 and the operation portion 30.

The longitudinal axis C shown in FIG. 1 and FIG. 3 is in a direction in which the insertion portion 20 and the distal configuration portion 25 are long, and indicates the axial direction of the insertion portion 20.

[Distal Configuration Portion 25]

As shown in FIG. 3, a proximal end portion of the distal configuration portion 25 is fitted into a joint ring 23a of the bendable portion 23 to couple the distal configuration portion 25 to the bendable portion 23. The distal configuration portion 25 has a body portion 100 made of a metal such as SUS, and a cover portion 120 which covers a circumferential surface of the body portion 100 and which has electric insulation. This distal configuration portion 25 has a laminated structure.

The joint ring 23a is covered with a cylindrical cover member 23b, and a distal end portion of the cover member 23b is watertightly fixed to the body portion 100 by a thread or by bonding.

As shown in FIG. 2A and FIG. 2B, a part of an outer circumferential surface of the distal configuration portion 25 is flattened, and a flat part is provided along the longitudinal axis C direction and divided into two parts in a direction that intersects at right angles with the longitudinal axis C direction. A flat observation surface portion 101 is formed in one part of the flat part. A step is provided between the observation surface portion 101 and the outer circumferential surface. A housing portion 107 which communicates with a distal opening portion 109 is formed in the other part of the flat part. The observation surface portion 101 is a flat surface portion exposed from the distal opening portion 109.

An illumination window portion 101a to emit the illumination light and an observation window portion 101b are disposed in the observation surface portion 101. The illumination window portion 101a and the observation window portion 101b are collinearly provided along the longitudinal axis C direction. The distal configuration portion 25 has an unshown image pickup device which is provided the inside of the distal configuration portion 25 and which faces the observation window portion 101b. A wall portion 103 which is a part of the cover portion 120 is provided in the vicinity of the observation surface portion 101. The wall portion 103 is provided to intersect at right angles with the observation surface portion 101, and is erected relative to the observation surface portion 101. A nozzle portion 103a is provided in the wall portion 103. The nozzle portion 103a blows a fluid including a washing solution such as physiological saline toward the illumination window portion 101a and the observation window portion 101b. The illumination window portion 101a and the observation window portion 101b are washed with the fluid. This observation surface portion 101 is a reference position (reference surface) for a second regulation portion 433 of a later-described positioning mechanism 430.

The distal opening portion 109 is provided in a side circumferential surface of the insertion portion 20. As shown in FIG. 3, the housing portion 107 opens toward the lateral side and outside of the distal configuration portion 25 via the distal opening portion 109. The swing table 201 is swingably housed and disposed in the housing portion 107.

[Swing Table 201]

The swing table 201 is rotatably supported by a raising shaft 201b, and coupled to a raising operation portion 200 via a pull-press member 211 which is a wire member. A distal end portion of the pull-press member 211 is coupled to the swing table 201, and a proximal end of the pull-press member 211 is coupled to the raising operation portion 200. The raising operation portion 200 is provided in the operation portion 30. By the operation of the raising operation portion 200, the swing table 201 rotates and is rises or falls, for example, 90 degrees or more. Specifically, the raising operation portion 200 pulls the pull-press member 211 by a pulling operation, and raises the swing table 201 via the pull-press member 211. The raising operation portion 200 presses the pull-press member 211 by a pressing operation, and causes the swing table 201 to fall via the pull-press member 211. Thus, the swing table 201 is housed in the housing portion 107 which communicates with the distal opening portion 109, and rotates in the housing portion 107 and thereby rises from the distal opening portion 109. The raising operation portion 200 operates the rotation of the swing table 201.

The swing table 201 may be not only a rising type but also a type that swings the treatment instrument right and left.

In the present embodiment, contamination such as bodily fluids and living tissue fragments adheres to, for example, the periphery of the raising shaft 201*b* and a part that is shadowed when seen from the housing portion 107. These parts are, for example, a back surface of the swing table 201, and the part between the back surface of the swing table 201 and the cover portion 120. The swing table 201 and a drive mechanism (e.g. the pull-press member 211) of the swing table 201 are disposed the inside of the narrow housing portion 107. Thus, decontamination of the periphery of the raising shaft 201*b* and the above parts is difficult.

[Washing System 300]

Generally, for example, it is difficult for the fluid and a washing tool to reach the housing portion 107 including the part between the back surface of the fallen or raised swing table 201 and the cover portion 120. The fluid includes, for example, the washing solution and an antiseptic solution. The washing tool is, for example, a washing brush. When the fluid is used, the fluid is briskly supplied to the part between the back surface of the swing table 201 and the cover portion 120 from the distal opening portion 109.

Generally, various kinds of insertion devices 10 are prepared in accordance with specifications and purposes, and the insertion system 1 needs to have the washing system 300 prepared for each kind of insertion device 10. In other words, the washing system 300 is not common to all insertion devices 10, and as many washing systems 300 as the number of insertion devices 10 are prepared. As a result, the management of the washing systems 300 is not easy, and ensuring a storage space for the washing systems 300 is not easy. Thus, a washing system 300 which is easily managed and for which a storage space is easily ensured is requested. In the washing system 300 according to the present embodiment, part of the configuration of the washing system 300 is common to the insertion devices 10.

Figure 4:
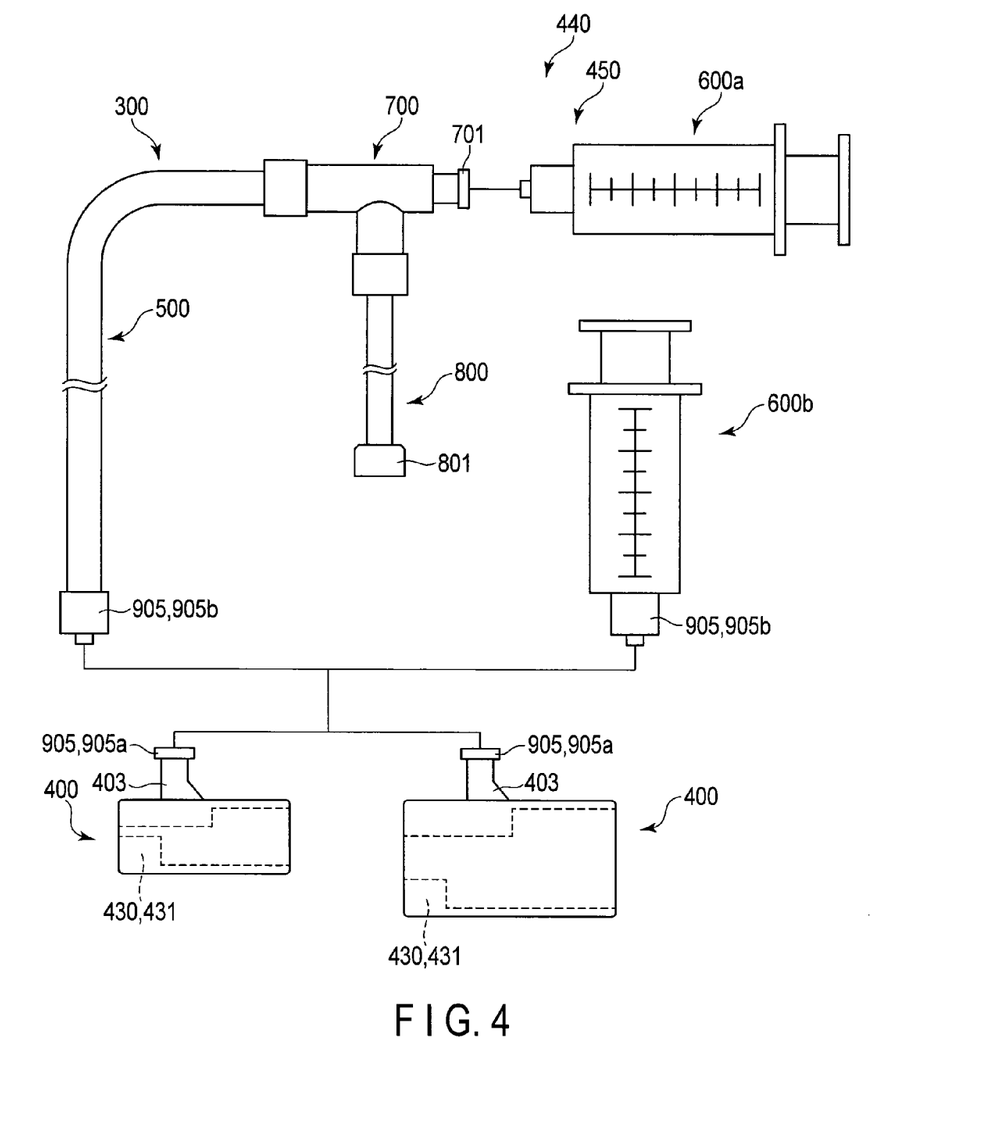
FIG. 4 is a schematic diagram of a washing system to wash a distal end portion of an insertion portion provided in the insertion system.

The washing system 300 shown in FIG. 4 washes the insertion portion 20 having the distal opening portion 109 provided in the distal-side circumferential surface of the insertion portion 20. As shown in FIG. 4, the washing system 300 has the cylindrical body portion 400 which is prepared for each kind of insertion portion 20 and which houses the distal end portion of the insertion portion 20, and a supply hole portion 403 which provided in a thick portion of the body portion 400 to communicate with the inside of the body portion 400. The kind indicates at least one of, for example, the shape, the size, and the specification and purpose. As shown in FIG. 4, the washing system 300 has a supply mechanism 440 which is shared by the body portion 400 corresponding to each insertion portion 20 that is prepared and which supplies the fluid to the supply hole portion 403 and which is attachable to and detachable from the supply hole portion 403.

[Body Portion 400]

Figure 5A:
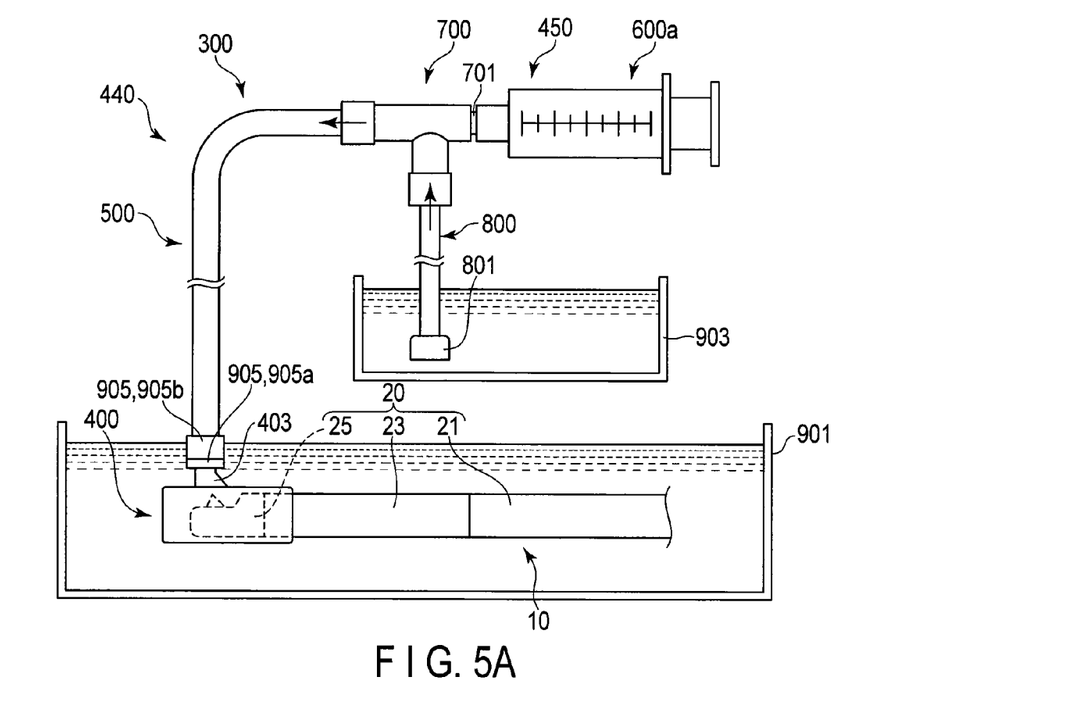
FIG. 5A is a diagram showing the insertion portion including the distal end portion to which a body portion is attached in a state where a supply member provided in the washing system is attached to the body portion provided in the washing system.
Figure 5B:
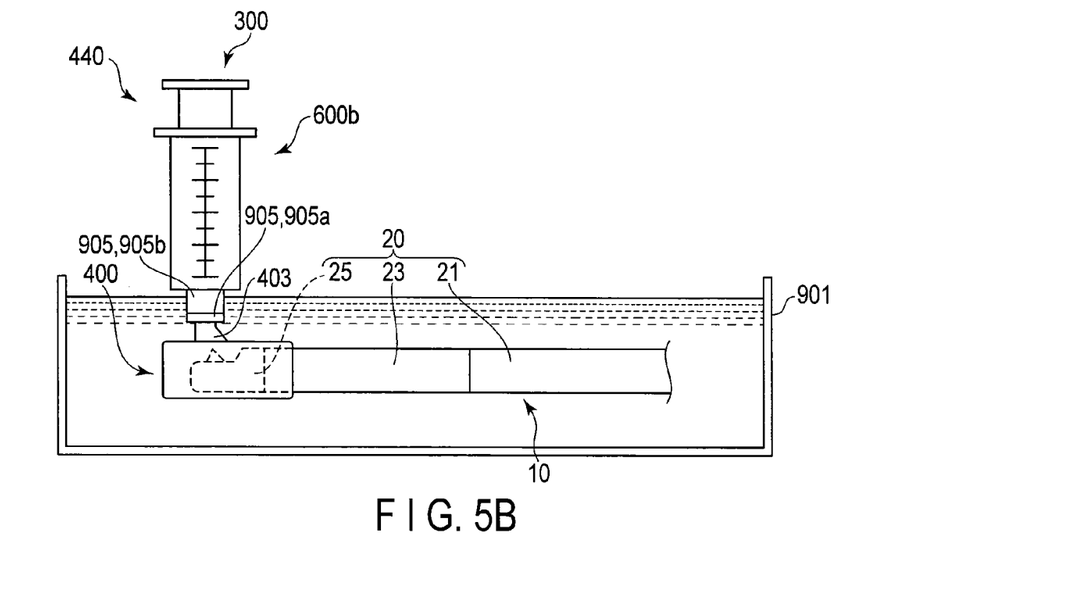
FIG. 5B is a diagram showing the insertion portion including the distal end portion to which the body portion is attached in a state where a supply source provided in the washing system is attached to the body portion.

The body portion 400 shown in FIG. 4, FIG. 5A, and FIG. 5B is attached to the distal configuration portion 25 when, for example, the distal configuration portion 25 which is the distal end portion of the insertion portion 20 where the distal opening portion 109 is provided is inserted into the body portion 400. When the distal configuration portion 25 is inserted into the body portion 400, the distal configuration portion 25 is housed in the body portion 400. When the distal configuration portion 25 is pulled out of the body portion 400, the body portion 400 is removed from the distal configuration portion 25. Thus, the body portion 400 is attachable to and detachable from (insertable into and removable from) the distal configuration portion 25.

In the present embodiment, at least one body portion 400 is prepared in accordance with the kind of insertion portion 20 that is prepared. Specifically, more than one body portion 400 are prepared in accordance with the kind of distal configuration portion 25 that is prepared. For example, even when more than one distal configuration portion 25 have the same shape, the body portion 400 is prepared for each of the distal configuration portions 25 if the distal configuration portions 25 are different in size from each other. The body portions 400 are replaceable for the distal configuration portions 25. The prepared body portions 400 are selected suitably to, for example, an operative method and the kind of endoscope that is used. The respective inside diameters of the body portions 400 are different from each other in accordance with the kinds of distal configuration portions 25 to which the body portions 400 are attached. This also holds true with the outside diameters.

The body portion 400 has, for example, a circular cylindrical shape. As shown in FIG. 6C, both end portions of the body portion 400 are open.

Figure 6A:
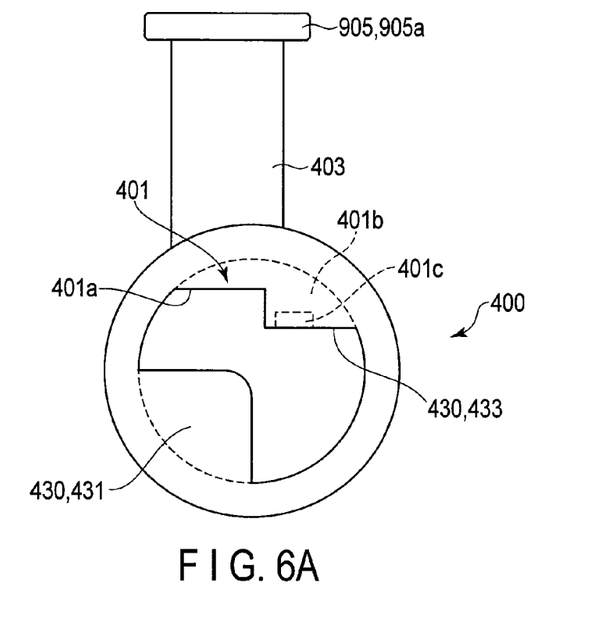
FIG. 6A is a diagram in which the body portion is seen from the distal side of the body portion.
Figure 6B:
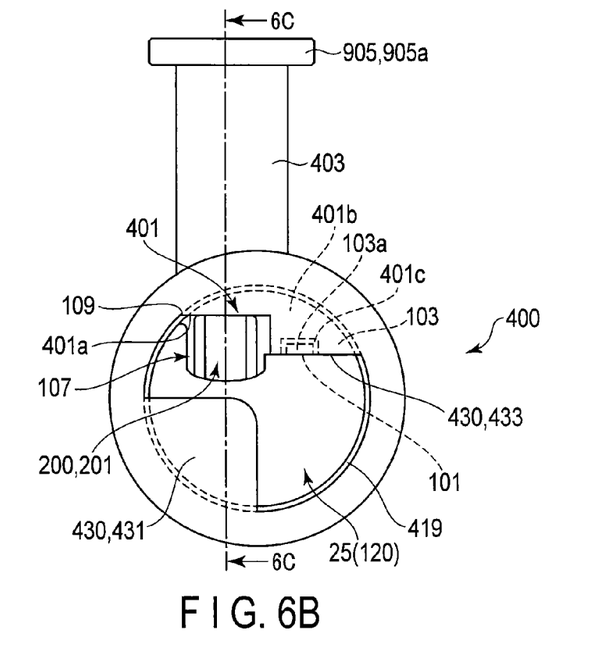
FIG. 6B is a diagram in which the body portion attached to the distal end portion of the insertion portion is seen from the distal side of the body portion.
Figure 6C:
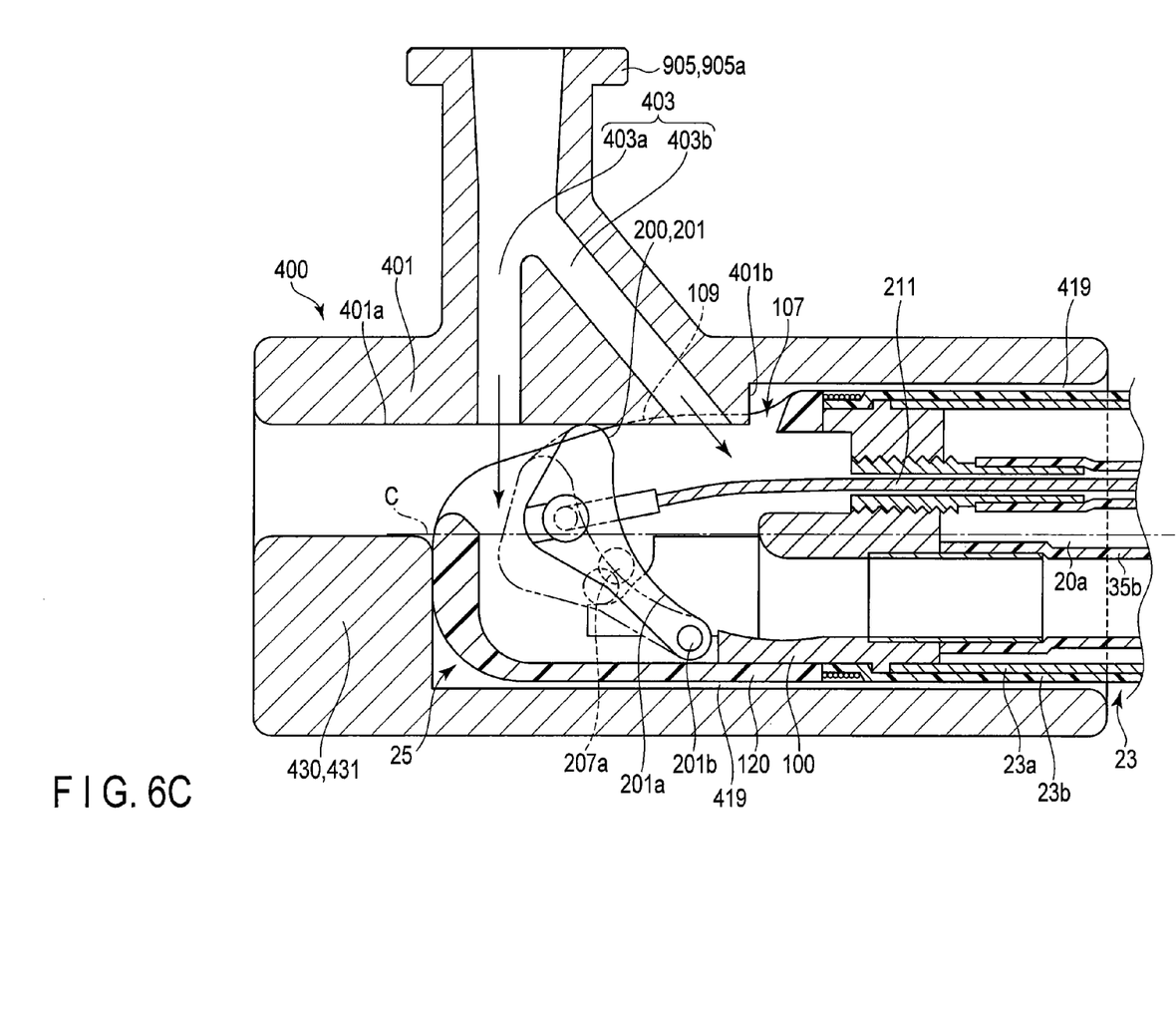
FIG. 6C is a sectional view taken along the line 6C-6C shown in FIG. 6B.

As shown in FIG. 6A, FIG. 6B, and FIG. 6C, the body portion 400 has a protruding portion 401 which is formed by the protrusion of a part of an inner circumferential surface of the body portion 400 toward the inside of the body portion 400. The protruding portion 401 has such a height that a tip portion of the swing table 201 abuts on a planar portion 401*a* of the protruding portion 401 when the swing table 201 rises at an angle between a maximum rising angle and a maximum falling angle. The swing table 201 regulates a movement of the insertion portion 20 relative to the body portion 400 in a insertion direction of the insertion portion 20, and regulates a movement of the insertion portion 20 relative to the body portion 400 in a direction around an axis of the insertion portion 20, by the abutment of the swing table 201 with the planar portion 401*a* which is the inner circumferential surface. In other words, the body portion 400 and the distal configuration portion 25 are positioned relative to each other in the insertion direction and in the direction around the axis by the abutment of the swing table 201 with the planar portion 401*a*.

Thus, the planar portion 401*a* and the swing table 201 position the body portion 400 and the distal configuration portion 25 relative to each other in the insertion direction and in the direction around the axis. The body portion 400 is then attached to the distal configuration portion 25 in a positioned state.

As shown in FIG. 6C, the planar portion 401*a* is provided along the insertion-removal direction of the distal configuration portion 25 relative to the body portion 400, and provided parallel to the longitudinal axis C.

For example, at the tip portion of the swing table 201 which is a part farthest from the raising shaft 201*b*, the part that abuts on the planar portion 401*a* is, for example, a tip portion of a guide surface 201*a*.

As shown in FIG. 6C, the swing table 201 is limited in rising angle by the abutment of the swing table 201 with the planar portion 401*a*.

As shown in FIG. 6A and FIG. 6B, the protruding portion 401 has a nozzle cover portion 401*c* which is provided in a back surface 401*b* of the protruding portion 401 and covers the nozzle portion 103*a* by the abutment of the nozzle portion 103*a* when the body portion 400 is attached to the distal configuration portion 25 as described above.

As shown in FIG. 2A and FIG. 6B, the body portion 400 is positioned relative to the distal configuration portion 25 in the insertion direction by the abutment of the wall portion 103 with the back surface 401b.

As shown in FIG. 6A, FIG. 6B, and FIG. 6C, the body portion 400 has the positioning mechanism 430 which positions the distal end portion of the insertion portion 20 relative to the body portion 400 so that the distal opening portion 109 is provided collinearly with the supply hole portion 403 in a direction that intersects at right angles with the insertion direction of the insertion portion 20.

As shown in FIG. 6A, FIG. 6B, and FIG. 6C, the positioning mechanism 430 has a first regulation portion 431 on which a distal end portion of the cover portion 120 at the distal end portion of the insertion portion 20 abuts when the body portion 400 houses the distal end portion of the insertion portion 20 as described above and which regulates the movement of the insertion portion 20 relative to the body portion 400 in the insertion direction of the insertion portion 20 by the abutment.

As shown in FIG. 6C, the first regulation portion 431 is provided, for example, opposite to the protruding portion 401 in a diametrical direction of the body portion 400. The first regulation portion 431 is formed as a protruding portion which is formed by the protrusion of, for example, a part of the inner circumferential surface of the body portion 400 toward the inside of the body portion 400. The first regulation portion 431 functions as, for example, a wall portion which is provided more on the front side than the distal end of the cover portion 120 in the insertion direction and on which the distal end of the cover portion 120 abuts. The first regulation portion 431 is integral with the body portion 400, but may be separate therefrom.

The timing of the first regulation portion 431 to abut on the distal end portion of the cover portion 120 is the same as, for example, the timing of the wall portion 103 to abut on the back surface 401b. One of the abutment of the first regulation portion 431 with the distal end portion of the cover portion 120 and the abutment of the wall portion 103 with the back surface 401b may take place first.

As shown in FIG. 6A and FIG. 6B, the positioning mechanism 430 has the second regulation portion 433 on which the observation surface portion 101 at the distal end portion of the insertion portion 20 abuts when the body portion 400 houses the distal end portion of the insertion portion 20 as described above and which regulates the movement of the insertion portion 20 relative to the body portion 400 in the direction around the axis of the insertion portion 20 by the abutment.

The second regulation portion 433 is provided at a position different from that of the first regulation portion 431. The second regulation portion 433 is, for example, provided more on the back side than the first regulation portion 431 in the insertion direction. The second regulation portion 433 is formed as a wall portion which is formed by the protrusion of a part of the inner circumferential surface of the body portion 400 toward the inside of the body portion 400 and on which the observation surface portion 101 that is a planar portion abuts. The second regulation portion 433 is a planar portion provided in the protruding portion 401, and is adjacent to the planar portion 401a and protrudes to the lower side (the inside of the body portion 400) more than the planar portion 401a.

As shown in FIG. 6C, this positioning mechanism 430 positions the distal end portion of the insertion portion 20 relative to the body portion 400 so that the supply hole portion 403 supplies the fluid to between the raised swing table 201 and the distal end portion of the insertion portion 20, specifically, to between the raised swing table 201 and the distal end of the cover portion 120 and to the distal end portion of the pull-press member 211.

To be specific, the positioning mechanism 430 positions the distal end portion of the insertion portion 20 relative to the body portion 400 so that a distal end portion of a later-described first supply hole portion 403a opens toward between the swing table 201 and the distal end of the cover portion 120 and a distal end portion of a second supply hole portion 403b opens toward the distal end portion of the pull-press member 211 when the distal end of the cover portion 120 abuts on the first regulation portion 431, the observation surface portion 101 abuts on the second regulation portion 433, the wall portion 103 abuts on the back surface 401b, and the swing table 201 abuts on the planar portion 401a.

[Supply Hole Portion 403]

As shown in FIG. 6C, the supply hole portion 403 supplies the fluid to the distal opening portion 109 of the insertion portion 20 housed in the body portion 400.

As shown in FIG. 6C, the supply hole portion 403 is integral with, for example, the body portion 400. As shown in FIG. 4, one end portion of the supply hole portion 403 protrudes outward from the body portion 400. This end portion is attachable to and detachable from a supply member 500 so that the end portion communicates with the supply member 500 of the body portion 400. This end portion is also attachable to and detachable from a supply source 600b so that the end communicates with the supply source 600b of the supply mechanism 440. The other end portion of the supply hole portion 403 is a portion which is divided into two parts and is, for example, y-shaped.

As shown in FIG. 6C, in a state where the swing table 201 is in abutment with the protruding portion 401, a distal end portion of the first supply hole portion 403a of the supply hole portion 403 opens toward between the swing table 201 and the distal end of the cover portion 120 in the axial direction of the first supply hole portion 403a. In this state, a distal end portion of the second supply hole portion 403b of the supply hole portion 403 opens toward the distal end portion of the pull-press member 211 in the axial direction of the second supply hole portion 403b. Thus, the supply hole portion 403 is provided on the front and back side of the swing table 201 in the insertion-removal direction of the distal configuration portion 25.

The distal end portion of the second supply hole portion 403b is provided more on the outer side than the distal end portion of the first supply hole portion 403a in the diametrical direction of the body portion 400, and provided on the back surface 401b side of the protruding portion 401.

A proximal end portion of the second supply hole portion 403b joins the first supply hole portion 403a. A proximal end portion of the first supply hole portion 403a is provided along the diametrical direction of the body portion 400, and communicates with the supply member 500 or the supply source 600b. By way of example, the first supply hole portion 403a is provided along the diametrical direction of the body portion 400, i.e., at right angles with the axial direction of the body portion 400. The second supply hole portion 403b is inclined relative to the first supply hole portion 403a.

To be specific, the second supply hole portion 403b is inclined, for example, at an acute angle relative to a direction that intersects at right angles with the axial direction of the body portion 400.

Although not shown, the second supply hole portion 403b may be formed from the central axis of the body portion 400 toward the side surface of the body portion 400 when the second supply hole portion 403*b* is seen from above.

Thus, a flow path portion for the fluid has one supply mechanism 440, and the supply hole portion 403 having the first supply hole portion 403*a* and the second supply hole portion 403*b*.

The body portion 400 is made of, for example, a transparent material so that the condition of washing can be judged from the outside. The inner shape of the body portion 400 is larger than the outer shape of the distal configuration portion 25. Thus, when the body portion 400 is attached to the distal configuration portion 25, a clearance portion 419 is formed between the body portion 400 and the distal configuration portion 25. Both end portions of the body portion 400 are open. The clearance portion 419 and the open both end portions function as the flow path portion to allow the fluid to flow to the outside of the body portion 400. The clearance portion 419 and the open both end portions ensure that the fluid is discharged to the outside of the body portion 400.

[Supply Mechanism 440]

As shown in FIG. 4, FIG. 5A, and FIG. 5B, the supply mechanism 440 has at least one of a unit 450 having the cylindrical supply member 500 and a supply source 600*a*, and the single supply source 600*b*. The unit 450 has a coupling portion 700 to attach the supply source 600*a* to the supply member 500.

As shown in FIG. 4 and FIG. 5A, the supply member 500 is directly attachable to and detachable from the supply hole portion 403 so that the supply member 500 communicates with the inside of the body portion 400. The supply member 500 directly supplies the fluid to the supply hole portion 403. The supply member 500 functions as a tube extended from the coupling portion 700.

As shown in FIG. 4, FIG. 5A, and FIG. 5B, the supply source 600*a* has a syringe which is removably attached to the supply member 500 via the coupling portion 700 and which supplies the fluid to the supply member 500.

As shown in FIG. 4 and FIG. 5B, the supply source 600*b* has a syringe which is directly attachable to and detachable from the supply hole portion 403 and which directly supplies the fluid to the supply hole portion 403. If the supply source 600*b* is attachable to and detachable from an attachment opening portion 701 of the coupling portion 700, the supply source 600*b* can function as the supply source 600*a*. That is, the supply source 600*b* is the same member as the supply source 600*a*. The supply source 600*b* may be unattachable to the attachment opening portion 701 and may be a member different from the supply source 600*a*.

As shown in FIG. 4, FIG. 5A, and FIG. 5B, the supply member 500 and the supply source 600*b* are directly removably fixed to the body portion 400. In other words, the supply source 600*a* is indirectly removably fixed to the body portion 400 via the supply member 500, and the supply source 600*b* is directly removably fixed to the body portion 400. The supply member 500 and the supply source 600*b* are directly removably fixed to the supply hole portion 403.

Both the supply member 500 and the supply source 600*b* may be attachable to and undetachable from the body portion 400, or one of them may be attachable and detachable.

The supply sources 600*a* and 600*b* may have, for example, pumps.

[Coupling Portion 700]

Figure 7A:
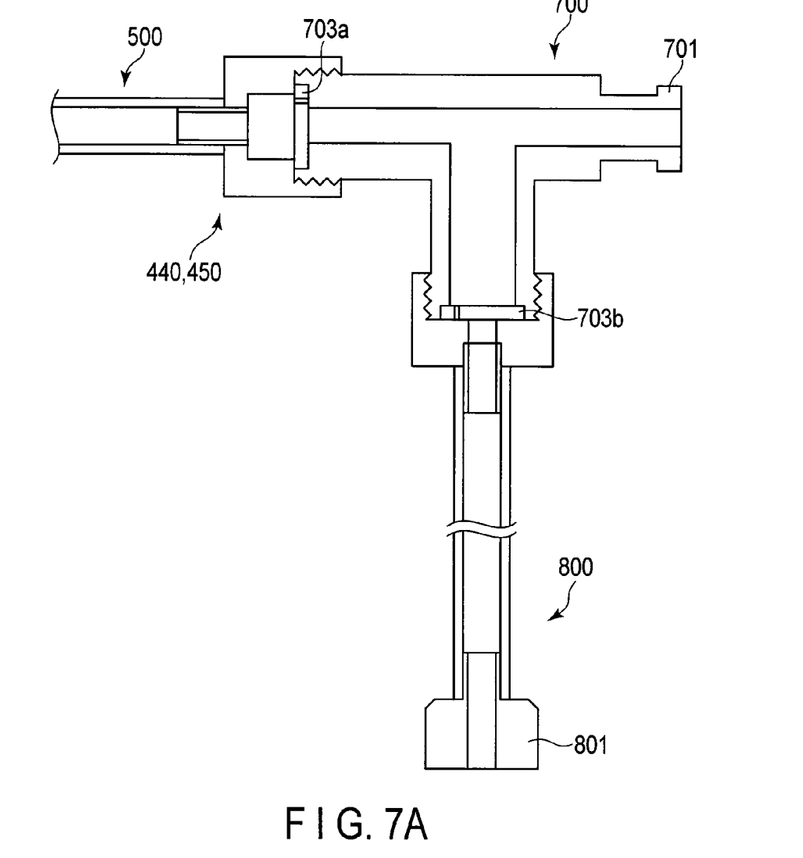
FIG. 7A is a diagram showing the structure of a coupling portion provided in the washing system.

As shown in FIG. 4 and FIG. 7A, the coupling portion 700 has the attachment opening portion 701 which is provided at a proximal end of the supply member 500 and to which the supply source 600*a* is attached.

As shown in FIG. 7A, the coupling portion 700 has a first check valve portion 703*a* and a second check valve portion 703*b* that are provided inside the coupling portion 700.

The first check valve portion 703*a* is provided at a junction potion of the coupling portion 700 and the supply member 500, and operates so that the fluid flows from the coupling portion 700 toward the supply member 500.

The second check valve portion 703*b* is provided at a junction portion of the coupling portion 700 and a suction member 800, and operates so that the fluid flows from the suction member 800 toward the coupling portion 700.

Figure 7B:
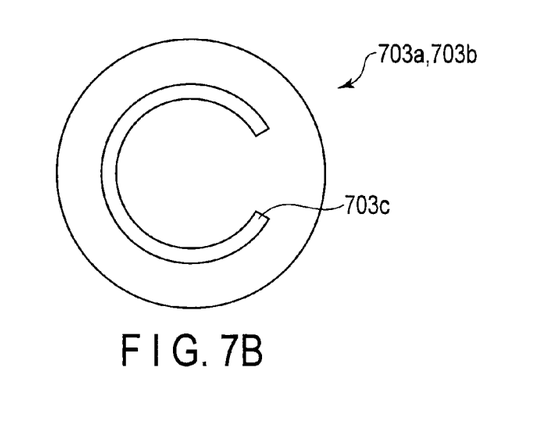
FIG. 7B is a diagram showing a check valve portion provided in the coupling portion.

As shown in FIG. 7B, the first check valve portion 703*a* and the second check valve portion 703*b* have, for example, a circular shape. The first check valve portion 703*a* and the second check valve portion 703*b* have C-shaped slit portions 703*c*.

The slit portions 703*c* pierce the first check valve portion 703*a* and the second check valve portion 703*b* in a thickness direction, and functions as a flow path in which the fluid flows.

As shown in FIG. 4, the coupling portion 700 has the cylindrical suction member 800 which functions as a tube extended from the coupling portion 700. A weight member 801 is provided at an end portion of the suction member 800.

[Fixing Mechanism 905]

As shown in FIG. 4, FIG. 5A, and FIG. 5B, the washing system 300 has a fixing mechanism 905 which is provided in the supply hole portion 403 and the supply mechanism 440 and which removably fixes the supply hole portion 403 and the supply mechanism 440 to each other. The fixing mechanism 905 has, but not limited in particular to, for example, a female cap portion 905*a* provided in the supply hole portion 403 and a male cap portion 905*b* provided in the supply member 500 and the supply source 600*b*. The cap portion 905*a* is connected to the cap portion 905*b*, for example, by screwing.

The first cap portion 905*a* may be provided in the supply member 500 and the supply source 600*b*, and the second cap portion 905*b* may be provided in the supply hole portion 403. That is, it is only necessary that the first cap portion 905*a* be provided in one of the supply hole portion 403 and the supply member 500 as well as the supply source 600*b*, the second cap portion 905*b* be provided in the other one, and the first cap portion 905*a* and the second cap portion 905*b* be removably fixable to each other.

It is appropriate that the cap portion 905*a* has a size common to all the body portions 400 regardless of the kinds of body portions 400. The cap portion 905*a* may be provided in the attachment opening portion 701.

Thus, one of the cap portion 905*a* and the cap portion 905*b* is provided in the supply hole portion 403, and the other one of the cap portion 905*a* and the cap portion 905*b* is provided in the supply mechanism 440.

[Functions]

The insertion portion 20 is inserted into a body cavity, and the insert object is inserted into the insertion portion 20 from the insertion opening portion 35*a*. The insert object is inserted through a channel 35*b* continuous with the insertion opening portion 35*a*, and inserted into the body cavity from the distal opening portion 109. When the raising operation portion 200 is operated, the swing table 201 rises or falls. Consequently, a rotation angle of the swing table 201 is adjusted, and the insert object comes closer to the affected area and observes or treats the affected area.

When the insertion portion 20 is inserted into the body cavity, the insertion portion 20 contacts contamination such as a bodily fluid. The contamination adheres to, for example, the swing table 201, the periphery of the raising shaft 201b, and the distal end portion of the pull-press member 211. Thus, these parts are previously washed with gauze and the washing tool after surgery. The insertion device 10 is then washed and sterilized by the washing system 300.

The distal configuration portion 25 is inserted into the body portion 400 until the wall portion 103 abuts on the back surface 401b, or the distal end of the cover portion 120 abuts on the first regulation portion 431, and the observation surface portion 101 abuts on the second regulation portion 433. The swing table 201 then rises at an angle between the maximum rising angle and the maximum falling angle, and the swing table 201 abuts on the planar portion 401a.

The distal end portion of the insertion portion 20 is positioned relative to the body portion 400 by the first regulation portion 431 and the second regulation portion 433 so that the distal end portion of the first supply hole portion 403a opens toward between the swing table 201 and the distal end of the cover portion 120 in the axial direction of the first supply hole portion 403a and the distal end portion of the second supply hole portion 403b opens toward the distal end portion of the pull-press member 211 in the axial direction of the second supply hole portion 403b.

In this instance, in the insertion direction of the insertion portion 20, the movement of the insertion portion 20 relative to the body portion 400 is regulated by the first regulation portion 431. In the direction around the axis of the insertion portion 20, the movement of the insertion portion 20 relative to the body portion 400 is regulated by the second regulation portion 433. By the abutment of the swing table 201 with the planar portion 401a, the body portion 400 and the distal configuration portion 25 are positioned relative to each other in the insertion direction and in the direction around the axis. By the abutment of the nozzle cover portion 401c with the nozzle portion 103a, the body portion 400 is positioned relative to the distal configuration portion 25 in the insertion direction.

After the body portion 400 is attached to the distal configuration portion 25, the body portion 400 is sunk in a fluid such as water that fills a container 901 together with the insertion portion 20. The container 901 is made of, for example, a transparent material. The end portion of the suction member 800 including the weight member 801 is sunk in a fluid such as a washing solution that fills a container 903.

When the supply source 600a is attached to the attachment opening portion 701 and the syringe of the supply source 600a is pulled as shown in FIG. 5A, the fluid that fills the container 903 is sucked via the suction member 800. When the syringe of the supply source 600a is then press, the sucked fluid is briskly supplied to the housing portion 107 via the supply member 500 and the supply hole portion 403.

To be specific, the fluid is briskly supplied to between the back surface of the swing table 201 and the cover portion 120 from the distal end portion of the first supply hole portion 403a, and briskly supplied to the distal end portion of the pull-press member 211 from the distal end portion of the second supply hole portion 403b. The supplied fluid is prevented from spattering by the inner circumferential surface of the body portion 400, and flows into the container 901 from both end portions of the body portion 400 via the clearance portion 419.

If the aforementioned operation is repeated, the contamination is removed, and the housing portion 107, a space between the raised swing table 201 and the distal end of the insertion portion 20, the swing table 201, the periphery of the raising shaft 201b, and the distal end portion of the pull-press member 211 are washed.

The contents described above are substantially similar even when the supply source 600b is directly attached to the supply hole portion 403.

The body portion 400 is replaceable in accordance with the kind of distal configuration portion 25, and prepared in accordance with the kind of distal configuration portion 25. However, the supply mechanism 440 is shared by the body portions 400 corresponding to the insertion portions 20 that are prepared, and at least the supply source 600b alone has only to be prepared. Thus, the management of the washing system 300 is easy, and ensuring a storage space for the washing system 300 is easy.

Advantageous Effects

In the present embodiment, the supply mechanism 440 can be common to the body portions 400. Thus, the present embodiment can provide the washing system 300 which is easily managed and for which a storage space is easily ensured.

In the present embodiment, the supply mechanism 440 has at least one of the unit 450 having the supply member 500 and the supply source 600a, and the single supply source 600b. Thus, in the present embodiment, the washing method can be varied.

In the present embodiment, the supply source 600a is the same member as the supply source 600b. Thus, the number of components can be reduced, management can be easier, and a storage space can be more easily ensured.

In the present embodiment, the supply member 500 and the supply source 600b can be detachable from the supply hole portion 403 by the fixing mechanism 905. Therefore, in the present embodiment, the body portion 400 and the supply mechanism 440 can be separately managed and stored, and a storage space can be easily ensured.

In the present embodiment, the distal opening portion 109 can be provided collinearly with the supply hole portion 403 in the direction that intersects at right angles with the insertion direction of the insertion portion 20 by the positioning mechanism 430.

In the present embodiment, the movement of the insertion portion 20 relative to the body portion 400 in the insertion direction of the insertion portion 20 can be regulated by the first regulation portion 431.

In the present embodiment, the movement of the insertion portion 20 relative to the body portion 400 in the direction around the axis of the insertion portion 20 can be regulated by the second regulation portion 433.

Thus, the fluid can be supplied without waste to contaminated parts such as the housing portion 107, the space between the raised swing table 201 and the distal end of the insertion portion 20, the swing table 201, the periphery of the raising shaft 201b, and the distal end portion of the pull-press member 211, and these parts can be efficiently washed.

In the present embodiment, by the positioning mechanism 430, the supply hole portion 403 can supply the fluid to the space between the raised swing table 201 and the distal end of the insertion portion 20 and to the distal end portion of the pull-press member 211.

In the present embodiment, when the swing table 201 rises at an angle between the maximum rising angle and the maximum falling angle, the swing table 201 abuts on the planar portion 401a. Accordingly, the movement of the insertion portion 20 relative to the body portion 400 in the insertion direction of the insertion portion 20 can be regulated, and the movement of the insertion portion 20 relative to the body portion 400 in the direction around the axis of the insertion portion 20 can be regulated. Thus, the fluid can be supplied without waste, and efficient washing can be conducted.

In the present embodiment, because the body portion 400 has a cylindrical shape, the fluid can flow to the container 901 from both end portions of the body portion 400.

In the present embodiment, the body portion 400 can be easily attached, and positioned and fixed to the distal configuration portion 25 by the nozzle cover portion 401c, the protruding portion 401, and the positioning mechanism 430 so that the distal end portion of the first supply hole portion 403a opens toward between the swing table 201 and the distal end of the cover portion 120 and so that the distal end portion of the second supply hole portion 403b opens toward the pull-press member 211.

In the present embodiment, when the body portion 400 is attached to the distal configuration portion 25, the swing table 201 rises at an angle between the maximum rising angle and the maximum falling angle. Thus, the fluid can be supplied even to the periphery of a regulation member 207a which regulates the swinging of the swing table 201, and the periphery of the regulation member 207a can be efficiently washed. The regulation member 207a is provided in a side surface of the swing table 201, and moves in response to the rotation of the swing table 201. The regulation member 207a is a rod-like member which is provided parallel to, for example, the raising shaft 201b and which can rotate around an axis of the regulation member 207a. The regulation member 207a abuts on a predetermined part in response to the rising of the swing table 201, and abuts on another predetermined part in response to the falling of the swing table 201. As a result of this abutment, the regulation member 207a regulates the rotation range of the swing table 201.

The regulation member 207a is provided at a position farthest from the distal opening portion 109. It is therefore possible to increase washing performance by supplying the fluid even to the periphery of the regulation member 207a with high pressure more than once.

In the present embodiment, the pull-press member 211 is substantially linear, and most of the outer circumferential surface of the distal end portion of the pull-press member 211 is exposed. Thus, in the present embodiment, the circumference of the distal end portion of the pull-press member 211 can also be easily washed together.

When the fluid is supplied to the distal configuration portion 25 from the second supply hole portion 403b, a force to remove the distal configuration portion 25 from the body portion 400 is applied to the distal configuration portion 25 by the flow pressure of the supplied fluid. However, in the present embodiment, because the swing table 201 abuts on the planar portion 401a, it is possible to prevent the distal configuration portion 25 from being removing from the body portion 400.

In the present embodiment, the first supply hole portion 403a ensures that the back surface of the swing table 201 and between the back surface of the swing table 201 and the distal end portion of the cover portion 120 can be washed. The periphery of the distal end portion of the pull-press member 211 can be washed by the second supply hole portion 403b.

In the present embodiment, it is possible to repetitively supply the fluid in high volume with ease only by operating the supply sources 600a and 600b.

In the present embodiment, because the body portion 400 is made of a transparent material, the condition of washing can be visually observed.

In the present embodiment, the clearance portion 419 is formed. This ensures that the fluid can be supplied even to the outer circumferential surface of the distal configuration portion 25 via the clearance portion 419, and the outer circumferential surface of the distal configuration portion 25 can also be washed.

In the present embodiment, the clearance portion 419 ensures that the fluid can flow to the outside of the body portion 400, and retaining of the fluid in the body portion 400 can be further prevented.

In the present embodiment, the nozzle cover portion 401c covers the nozzle portion 103a when the wall portion 103 abuts on the back surface 401b. It is therefore possible to prevent the fluid from clogging the nozzle portion 103a.

In the present embodiment, the washing system 300 including the body portion 400 is applicable not only to the insertion portion 20 of an endoscope but also to the insertion portion 20 of the insertion device 10, for example, a catheter or an over tube.

The present invention is not completely limited to the embodiment described above, and modifications of components can be made at the stage of carrying out the invention without departing from the spirit thereof. Various inventions can be made by properly combining the components disclosed in the embodiment described above.

What is claimed is:

1. A washing system to wash an insertion portion of an insertion device, the insertion device having an opening provided in a distal-side circumferential surface of the insertion portion, the washing system comprising:
    a body configured to house a distal end of the insertion portion, the body having a positioning mechanism to position the distal end of the insertion portion in a state where a swing table, that is provided at the distal end and that rises from the opening, is actuated to abut on an inner circumferential surface of the body;
    a supply hole provided in the body to communicate with the inside of the body, the supply hole supplying a fluid to the opening of the insertion portion housed in the body; and
    a supply mechanism which supplies the fluid to the supply hole and which is attachable to and detachable from the supply hole;
    wherein the supply hole is divided into two parts, each of the two parts being configured to supply the fluid to two parts in the opening, the two parts in the opening being different from each other.

2. The washing system according to claim 1, wherein the body comprises a plurality of bodies, each configured to house a different insertion portion.

3. The washing system according to claim 2, further comprising a fixing mechanism comprising:
    a first cap provided in one of the supply hole and the supply mechanism, and
    a second cap provided in an other one of the supply hole and the supply mechanism, the second cap being removably fixed to the first cap.

4. The washing system according to claim 1, wherein the supply mechanism comprises at least one of
    a unit comprising a cylindrical supply member which is directly attachable to and detachable from the supply hole and which supplies the fluid to the supply hole, and a supply source which is removably attached to the supply member and which supplies the fluid to the supply member, and a single supply source which is directly attachable to and detachable from the supply hole and which directly supplies the fluid to the supply hole.

5. The washing system according to claim 1, wherein the positioning mechanism of the body positions the distal end of the insertion portion relative to the body so that the opening is provided collinearly with the supply hole in a direction that intersects at right angles with an insertion direction of the insertion portion.

6. The washing system according to claim 5, wherein the positioning mechanism comprises a first regulation portion which regulates a movement of the insertion portion relative to the body in the insertion direction of the insertion portion by an abutment of the distal end of the insertion portion when the body houses the distal end of the insertion portion, and a second regulation portion which regulates a movement of the insertion portion relative to the body in a direction around an axis of the insertion portion by the abutment of the distal end of the insertion portion when the body houses the distal end of the insertion portion.

7. The washing system according to claim 1, further comprising a raising operation portion which actuates the swing table, wherein the positioning mechanism positions the distal end of the insertion portion relative to the body so that one of the two parts supplies the fluid to between the swing table actuated by the raising operation portion and the distal end of the insertion portion.

8. A washing method to wash an insertion portion of an insertion device, the insertion portion having an opening provided in a distal-side circumferential surface of the insertion portion, the washing method comprising:

housing a distal end of the insertion portion in a cylindrical body;

positioning the distal end of the insertion portion relative to the body by a positioning mechanism in a state where a swing table, that is provided at the distal end and that rises from the opening, is actuated to abut on an inner circumferential surface of the body; and supplying a fluid to the body by a supply mechanism, wherein the fluid is supplied to the opening of the insertion portion housed in the body by a supply hole which allows the supply mechanism to be attachable thereto and detachable therefrom and to which the fluid is supplied from the supply mechanism and which is provided in the body to communicate with the inside of the body, and the insertion portion is washed; and the supply hole is divided into two parts, each of the two parts being configured to supply the fluid to two parts in the opening, the two parts in the opening being different from each other.

* * * * *